United States Patent [19]

Schuler et al.

[11] Patent Number: 5,010,011

[45] Date of Patent: * Apr. 23, 1991

[54] BOVINE PLACENTAL LACTOGEN GENE

[75] Inventors: Linda A. Schuler, Madison; Jack Gorski, Middleton, both of Wis.; Walter L. Hurley, Urbana, Ill.; Robert D. Bremel, Madison, Wis.; Fritz M. Rottman, Pepper Pike, Ohio

[73] Assignee: Wisconsin Alumni Research Foundation, Madison, Wis.

[*] Notice: The portion of the term of this patent subsequent to Aug. 30, 2005 has been disclaimed.

[21] Appl. No.: 184,901

[22] Filed: Apr. 21, 1988

Related U.S. Application Data

[63] Continuation-in-part of Ser. No. 717,078, Mar. 28, 1985, Pat. No. 4,767,711.

[51] Int. Cl.$^5$ .................. C12N 15/00; C12N 15/16; C12N 15/63
[52] U.S. Cl. .................. 435/252.3; 435/69.4; 435/172.3; 435/243; 435/252.33; 435/320.1; 530/27; 935/13; 935/72; 935/73
[58] Field of Search ............. 435/69.4, 172.1, 172.3, 435/252.3, 252.31-252.35, 320, 243; 536/27; 935/13, 29, 72, 73

[56] References Cited

U.S. PATENT DOCUMENTS

| | | | |
|---|---|---|---|
| 4,332,892 | 6/1982 | Ptashne et al. | 435/69.7 |
| 4,363,877 | 12/1982 | Goodman et al. | 435/320 |
| 4,407,948 | 10/1983 | Goodman et al. | 435/91 |
| 4,419,446 | 12/1983 | Howley et al. | 435/69.1 |
| 4,767,711 | 8/1988 | Schuler et al. | 435/252.3 |

FOREIGN PATENT DOCUMENTS

0306470 8/1989 European Pat. Off. ......... 435/172.3

OTHER PUBLICATIONS

L. Schuler et al., 68th Meeting of Endocrine Society, Abstract 435 (1986).
L. Schuler et al., 67th Meeting of Endocrine Society, Abstract 528 (1985).
L. Schuler et al., 7th International Congress of Endocrinology, Abstract submittal, abstract published 1984.
W. L. Hurley et al., 64th Meeting of Endocrine Society, Abstract 851 (1982).
L. Schuler et al., Proc. Natl. Acad. Sci. USA 84: 5650-5654 (Aug. 1987).
K. A. Eakle et al., Endocrinology 110: 1758-1765 (1982).
G. Murthy et al., Endocrinology 111: 2117-2124 (1982).
Y. Arima et al., Endocrinology 113: 2186-2194 (1983).
J. Byatt et al., Endocrinology 119: 1343-1350 (1986).
N. L. Sasavage et al., J. Biol. Chem. 257: 678-681 (1982).
V. Glisin et al., Biochemistry 13: 2633-2637 (1974).
J. Sala — Trepet et al., Biochem. Biophys. Act. 519: 173-193 (1978).
H. Land et al., Nucl. Acid Res. 9: 2251-2266 (1981).
T. Maniatis et al., "Molecular Cloning, A Laboratory Manual", 229-246 Cold Spring Harbor (1982).
W. Miller et al., DNA 1: 37-50 (1981).
E. M. Southern, J. Mol. Biol. 98: 503-517 (1975).
R. Woychik et al., Nucl. Acids Res. 10: 7197-7210 (1982).
S. L. Berger et al., Meth. Enzym. 79: 59-68 (1981).
T. Hurley et al., Biochemistry 16: 5598-5604 (1977).
C. Schellenberg et al., Endocrinology 111: 2125-2128 (1982).
Arima et al., Chemical Abstracts 100: 17977e (1984).
Schuler et al., Biochemistry 27: 8443-8448 (1988).

*Primary Examiner*—James Martinell
*Attorney, Agent, or Firm*—Quarles & Brady

[57] ABSTRACT

Portions of the genetic sequence coding for bovine placental lactogen are isolated and a cDNA variant of a bovine placental lactogen gene is then formed and isolated. Upon cloning of the cDNA gene sequence and culturing of a resulting host, large quantities of bovine placental lactogen can be produced.

3 Claims, No Drawings

BOVINE PLACENTAL LACTOGEN GENE

This invention was made with government support under NIH Grant No. T32 HD07118 is awarded by the Department Of Health And Human Services and NSF Grant Nos. PCM 8409741 and PCM 8416415 awarded by the National Science Foundation. The Government has certain rights to this invention.

This is a continuation-in-part of U.S. Ser. No. 06/717,078, filed Mar. 28, 1985, now U.S. Pat. No. 4,767,711, issued Aug. 30, 1988.

BACKGROUND OF THE INVENTION

A. Field Of The Invention

The present invention relates to recombinant DNA technology. More specifically, it involves the creation of a cDNA genetic sequence coding for a bovine placental lactogen, a vector containing this gene, and a host containing the cDNA gene.

B. Description Of The Art

The placenta of a cow secretes numerous endocrine signals, including bovine placental lactogen (which is evolutionarily related to growth hormone and prolactin). Naturally produced bovine placental lactogen (also known as bovine chorionic somatomammotropin) has recently been purified and characterized. (See K. A. Eakle et al., Endocrinology 110:1758-1765 (1982); G. S. Murthy et al., Endocrinology 111:2117-2124 (1982); and Y. Arima et al., Endocrinology 113:2186-2194 (1983)) (the disclosure of these articles and of all other articles cited in this patent are incorporated by reference as a fully set forth below.) As described in these articles, at least one (and possibly three) forms of bovine placental lactogen exist.

Bovine placental lactogen promises to have great utility for research and other purposes. For example, it appears to relate to pregnancy development. (See generally C. Schellenberg et al., Endocrinology 111:2125-2128 (1982) (levels change during gestation), or it may stimulate milk production (see U.S. Pat. No. 3,644,925, bovine growth hormone increases milk production.) Still other functions for this protein are likely to be discovered.

Unfortunately, commercial qualities of the protein are not available, and it is prohibitively expensive to extract the protein from natural sources. Thus, it can be seen that a need has existed for a source of large quantities of bovine placental lactogen.

SUMMARY OF THE INVENTION

The present invention relates to a cDNA gene sequence, a recombinant vector, and a recombinant host. In one embodiment, there is provided a vector and a foreign cDNA gene sequence that codes for bovine placental lactogen which is inserted into the vector. cDNA is a gene coding for a protein, but with intervening sequences (introns) not coding for protein which might interfere with expression deleted. The bovine placental lactogen is one coded for by the bovine gene portion of pbPL1078.

pbPL1078 has been deposited at the American Type Culture Collection, Rockville, Md., in the recombinant host *E. coli* XL-1-Blue, with ATCC number 67631, and will be made available upon the issuance of this patent in accordance with U.S. patent law and other such foreign patent laws as may apply. The availability of this culture is not meant as a license to use it.

In another embodiment, there is provided a cDNA genetic sequence coding for bovine placental lactogen The sequence codes for a protein coded for by the bovine gene portion gene portion of pbPL1078.

In yet another embodiment, there is provided a recombinant host cell capable of expressing bovine placental lactogen. The host comprises a host cell, a promoter and a foreign cDNA gene sequence coding for bovine placental lactogen which is subjected to the promoter's control. Again, the bovine placental lactogen is one coded for by the bovine gene portion of pbPL1078. Preferably, the host can be cultured in a nutrient medium and grown up to large qualities.

Of course, it has been known for some time that genes code for proteins. It has also been known since the early 1970's that many genes can be made to express commercial quantities of a protein if the gene can be isolated and cloned. However, it is one thing to say this, and quite another to locate the specific gene which codes for a given protein. Further, in many cases one must form a cDNA variant of the gene before one can obtain expression of the protein.

Gene(s) which had previously defied identification and isolation were the bovine placental lactogen gene(s). A feature of the present invention, therefore, was the idea that if the bovine prolactin gene happened to be sufficiently similar to bovine placental lactogen gene, hybridization techniques might be able to identify the placental lactogen cDNA. However, this idea alone was not enough. Instead, an ingenious brick-by-brick approach was required.

Hybridization techniques work on the principle that under certain conditions dissimilar (but somewhat similar) DNA strands will hybridize (stick) together. The applicants discovered that given sufficient similarity in sequence, prolactin cDNA will hybridize to certain portions of the lactogen DNA gene, and then similar techniques could use these DNA fragments to pick out cDNA fragments, and then these cDNA fragments could pick out the lactogen cDNA. (It turns out that bovine prolactin cDNA won't readily hybridize directly to lactogen cDNA.) Thus, it took a very ingenious "brick by brick" approach to isolate the full lactogen cDNA. Further, once one bovine lactogen cDNA gene is located, it can be used in further hybridization comparisons to isolate other bovine lactogen cDNA.

The objects of the invention therefore include:

(a) providing a gene sequence that expresses a bovine placental lactogen;

(b) providing a cDNA bovine placental lactogen genetic sequence; and (c) providing vectors and hosts containing these sequences which permit the efficient commercial production of a bovine placental lactogen.

These and still other objects and advantages of the present invention will be apparent from the description which follows. These embodiments do not represent the full scope of the invention. Rather, the invention may be employed in other embodiments. Reference is therefore made to the claims herein for interpreting the scope of the present invention.

DESCRIPTION OF THE PREFERRED EMBODIMENTS

I. General Overview (a) We first screened a library of bovine genomic DNA prepared from fetal cotyledon using prolactin cDNA gene as a probe, and isolated small fragments of the lactogen DNA gene.

(b) We then inserted one such fragment of the bovine placental lactogen gene in a plasmid and grew-up large quantities of the DNA in an appropriate host.

(c) Separately, we converted a "soup" of bovine fetal cotyledon to a cDNA "soup".

(d) We then used the genomic fragment as a probe to find a cDNA fragment.

(e) We then used the cDNA fragment to find the longer cDNA.

(f) Once one full length cDNA was found, the cDNA was used to screen for other bovine placental lactogen.

II. Selection Of Prolactin Related Gene

To obtain genomic sequences similar to prolactin, a bovine genomic library from bovine fetal cotyledons was prepared. Construction and amplification of a bovine genomic library has been previously described (R. Woychik et al., Nucl. Acids Res. 10:7197-7210 (1982)). Briefly, bovine DNA fragments generated by partial Mbo I digestion are ligated into the Bam HI arms of the lambda phage Charon 28. The average genomic insert is about 14.5 kb.

When screened with a bovine prolactin cDNA (see N. L. Sasavage et al., J. Biol. Chem. 257:678-681 (1982)) at 32° C. and at 42° C. (50% formamide) appropriate lactogen gene segments can be isolated. The idea is that at low temperatures and high salt concentration sequences of even lesser homology (similarity) will stick together, whereas at higher temperatures and low salt concentrations sequences only stick to their own kind.

If a known sequence (e.g. the prolactin cDNA) is radio-labelled by nick translation, and hybridized to the bovine placental lactogen gene, using Southern hybridization techniques (E. M. Southern, J. Mol. Biol. 98:503-517 (1975)), parts of the bovine placental lactogen gene will stick to the labelled prolactin at one condition, yet separate at slightly higher temperature.

A gene fragment identified by this scheme (named bP04) hybridized to prolactin cDNA at 32° C., but not at 42° C. This indicated that bP04 contained some sequence homology to prolactin, but was not part of the prolactin gene. It should be noted that the bP04 did not significantly hybridize to bovine growth hormone cDNA at either 32° C. or 42° C.

A PstI restriction fragment of bP04 containing a part of the region with prolactin homology was cloned into the PstI site of pBR322 to yield pbPLgn04-3. As a confirmation that the fragment was not prolactin, the genomic insert from the plasmid was found to hybridize specifically to bovine placental poly(A)-containing RNA by RNA blotting, but not to bovine pituitary or liver RNA (prolactin hybridizes primarily to pituitary RNA).

The genomic insert was used to rescreen the genomic library under high stringency hybridization conditions (42° C., 50% formamide). Two further genomic clones were identified, bP12 and bP13.

III. Formation Of Bovine Placental cDNA "Soup"

Additional bovine fetal cotyledons were collected at time of slaughter, immediately frozen in liquid nitrogen, and then stored at −70° C. Frozen tissue was homogenized in a Tris/NaCl buffer containing 40 mM vanadyl-ribonucleoside complex (VRC, synthesized as described by S. L. Berger et al., Meth. Enzymology 79:59-68 (1981), and 1 mg/ml heparin as ribonuclease inhibitor).

The homogenate is deproteinated by repeated extraction with buffer saturated phenol and chloroform until the VRC color is gone. This is followed by an extraction with ether.

Crude bovine RNA is then separated by cesium chloride density gradient centrifugation (V. Glisin et al., Bio-chemistry 13:2633-2637 (1974)). Poly(A)-containing RNA is enriched from the RNA pellet by two passes on an oligo dT-cellulose affinity column. J. Sala-Trepet et al., Biochem. Biophys. Act 519:173-183 (1978).

To produce the cDNA from the RNA, one has two alternatives. One can use an S1 nuclease digestion step to cleave the hair-pin loop between first and second cDNA strands, and make both ends of the cDNA blunt-ended. However, this procedure often does not yield full-length sequences due to the S1 nuclease digestion. Another alternative for the second strand is similar to that described by H. Land et al., Nucl. Acid Res, 9:2251-2266 (1981). In this strategy, the first-strand synthesis reaction is analogous to the procedure of T. Maniatis et al., "Molecular Cloning, A Laboratory Manual". Pp 229-242 Cold Spring Harbor (1982) First-strand synthesis (changing the RNA to cDNA by reverse transcriptase) is primed with oligo dT. The reaction contains a human placental protein inhibitor of ribonuclease activity.

After first-strand synthesis, the reaction mixture is deproteinated with phenol:chloroform, the RNA base hydrolyzed, and the single-stranded cDNA purified by column chromatography. Single-stranded cDNA is tailed at the 3'-ends with dCTP using terminal deoxynucleotidyl transferase (TdT, H. Land et al., Nucl. Acids Res. 9:2251-2266 (1981). Oligo dG will be hybridized to the dC-tailed cDNA, providing a primer for second-strand synthesis.

Second-strand synthesis is an $E.\ coli$ polymerase I reaction, followed by a reverse transcriptase reaction similar to that used in the first-strand reaction. Using these enzymes sequentially gives maximal second-strand synthesis due to the presence of different stopping sequences in the template for the two enzymes (See T. Maniatis et al., supra).

The first-strand tailing step obviates need for a $S_1$ nuclease reaction, and the proportion of full-length sequences is maximized. Double-stranded cDNA is tailed with dCTP using TdT enzyme. Tailed, double-stranded cDNA is then sized by agarose gel electrophoresis, and DNA of lengths between given ranges, e.g. 1000 and 1200 bp, is extracted. (The mature lactogen message is believed to be between these ranges based on the m-RNA length.) This sizing step greatly increases the proportion of lactogen-containing clones and increases the efficiency of cDNA library screening. Sized, double-stranded cDNA are then annealed with Pst I cut, dG-tailed pBR322, and used to transform $E.\ coli$ strain HB101. Transformation is by a $CaCl_2$ method on tetracycline plates.

IV. Selection Of The cDNA Of Interest

Thus far, we have prepared a cDNA "soup" in part III, and a probe to help find the cDNA of interest in part II. The pbPLgn04-3 insert (the probe) is then used to screen a cDNA library.

To screen the cDNA colonies as described above, the colonies are transferred to 96-well microtiter plates containing L-broth plus tetracycline. Library screening uses a 96-well filter block where aliquots of each well are filtered onto nitrocellulose or GeneScreen (New England Nuclear) filters. The cells are lysed and the DNA fixed to the filter. Filters are washed extensively with a 2×SSC, 0.1% SDS solution to minimize hybridization background.

From 237 colonies screened, one specifically hybridized to the pbPLgn04-3 genomic insert. As a test, the cDNA (360 bp) specifically hybridized to bovine placental RNA (RNA blotting), but not to bovine pituitary or liver RNA. Thus, it was not a prolactin gene fragment.

To obtain a longer cDNA, a second library was constructed using only insert lengths of 600 to 1300 bp. This library was then screened with that cDNA fragment of 360 bp, specifically identifying 20 clones from 1650 recombinants screened. The longest of these was pbPL10 with an insert length of about 875 bp, believed to represent the full coding length. As a test, the pbPL10 insert was hybridized to RNA blots containing bovine placental, pituitary and liver RNA. As with the genomic fragment pbPLgn04-3 and the 360 bp cDNA, pbPL10 hybridized specifically to placental RNA.

Sequence analysis of the cDNA pBPL10, containing 777 bp of coding sequence and 98 bp of the 3' region, reveals strong homology to the sequence for bovine prolactin reported in N. L. Sasavage et al., J. Biol. Chem 257:678-681 (1982); W. Miller et al., DNA 1:37-50 (1981). These 875 bp are 74% homologous to prolactin cDNA at the level of nucleotide sequence. Translation of the sequence indicates 39% homology in the amino acid sequence of the two proteins.

V. Obtaining pbPL1078

To isolate the bovine placental lactogen gene coding for the protein described in K. A. Eakle et al., Endocrinology 100:1758-1765 (1982), the general strategy outlined above (i.e. using low stringency hybridization to bovine prolactin cDNA to identify related placental cDNAs) was used with the following modifications. A new bovine fetal placental cDNA library was constructed from poly (A)+RNA from about 6 months gestation in the vector lambda gt10. T. V. Huynh et al., "Constructing And Screening cDNA Libraries In Lambda gt10 And Lambda gt11", DNA Cloning, Vol. I: A Practical Approach, D. M. Glover, ed., IRL Press, pp 49-78 (1984) using the procedures outlined except that second strand synthesis was carried out in the presence of RNase H (U. Gubler et al., Gene, 25:263-269 (1983)), and mung bean nucleases (rather than S1 nuclease) was used to blunt-end the DNA prior to addition of EcoRI linkers.

105 recombinant plaques were lifted in duplicate to nylon hybridization membrane (ICN). One set was hybridized to bovine prolactin cDNA under conditions of lowered stringency (5×SSPE, 5×Denhardt's, 0.2% SDS at 60° C., followed by 3×15 min washes in 2×SSC, 0.2% SDS at 65° C.). The duplicate set was hybridized to other placental cDNA we have isolated (e.g. pbPL10 under conditions of high stringency (2.5×SSPE, 5×Denhardt's, 0.2% SDS at 68° C., followed by 1 hour wash in 2×SSC, 0.2% SDS at 68° C., and 1 hour wash in 0.1×SSC, 0.1%SDS at 68° C.).

Those clones which hybridized to bovine prolactin cDNA under conditions of lowered stringency but which were different from those already identified as shown by their failure to hybridize to those placental cDNAs under conditions of high stringency were then further analyzed by nucleotide sequence analysis. pbPL713 was identified in this fashion as coding for a portion of Eakle's bovine placental lactogen using protein sequence data. pbPL713, in turn, was used to locate pbPL1078 (which contains the full length gene).

VI. Expression Systems

The E. coli expression vector we are currently working with is that described by C. Queen, J. Mol. App. Gene. 2:1-10 (1983), the pCQV2 in the E. coli strain CHS-26. pbPL1078 can be transferred to the M13 vector "Phagescript" (Stratagene, San Diego), modified using site specific mutagenesis, and transferred en bloc to pCQV2 between the BamHI and SalI restriction sites, yielding an expression plasmid pLAS137. In this construct, expression of the cDNA by the strong lambda promoter (PR) is under control of the temperature sensitive repressor protein cI857. Once overproduction of the desired protein is achieved, it can be purified away from bacterial protein by a variety of established techniques.

Although the especially preferred embodiments of the invention have been described above, it should be noted that the invention is not so limited. In this regard, there may be various other modifications and changes to these embodiments that are within the scope of the invention. For example, it is expected that through use of conventional recombinant techniques various small modifications and changes in the genetic sequence (such as controllers, triggers, etc.) might also be possible.

Also, E. coli derivatives are obviously not the only possible hosts. Numerous other hosts suitable for storage and/or protein production are possible. It might also be noted that plasmids are not the only possible vectors. Other vectors (e.g. phages) might also be suitable. All such structures are to be deemed to be within the scope of the invention.

We claim:
1. A recombinant vector, comprising:
    a vector; and
    a foreign cDNA sequence coding for bovine placental lactogen which has been inserted into said vector; wherein the bovine placental lactogen is one coded for by a bovine gene portion of pbPL1078.
2. A cDNA sequence coding for bovine placental lactogen, wherein the sequence codes for a protein coded for by a bovine gene portion of pbPL1078.
3. A recombinant host cell capable of expressing bovine placental lactogen, comprising:
    a host cell
    a promoter; and
    a foreign cDNA gene sequence coding for bovine placental lactogen which is subjected to the control of the promoter, wherein the bovine placental lactogen is one coded for by a bovine gene portion of pbPL1078.

* * * * *